United States Patent
Penning et al.

Patent Number: 6,162,823
Date of Patent: Dec. 19, 2000

[54] LTA₄ HYDROLASE INHIBITORS

[75] Inventors: Thomas Dale Penning, Emhurst; Stella Siu-tzyy Yu, Morton Grove; James Malecha, Libertyville; Chi-Dean Liang, Glenview; Mark Andrew Russell, Gurnee, all of Ill.

[73] Assignee: G.D. Searle & Co., Chicago, Ill.

[21] Appl. No.: 08/815,700

[22] Filed: Mar. 12, 1997

[51] Int. Cl.⁷ .................. A61K 31/38; A61K 31/18; C07D 333/22; C07C 303/00

[52] U.S. Cl. .................. 514/438; 514/444; 514/445; 514/447; 514/604; 514/605; 514/365; 514/369; 514/370; 514/342; 514/255; 549/59; 549/68; 549/77; 564/91; 564/99; 548/187; 548/195; 548/198; 548/204; 546/280.4

[58] Field of Search .................. 564/91, 99; 514/604, 514/605, 444, 445, 447, 438, 342, 255, 365, 369, 370; 549/59, 68, 77; 548/187, 195, 198, 204, 205; 546/280.4; 544/379

[56] References Cited

U.S. PATENT DOCUMENTS

| | | | |
|---|---|---|---|
| 6,046,229 | 4/2000 | Chang et al. | 514/445 |
| 6,051,599 | 4/2000 | Elliot et al. | 514/444 |
| 6,063,928 | 5/2000 | Stevens et al. | 546/269.7 |

FOREIGN PATENT DOCUMENTS

| | | |
|---|---|---|
| 287959 | 10/1988 | European Pat. Off. |
| 4121849 | 1/1993 | Germany |
| WO9610999 | 4/1996 | WIPO |
| WO9611192 | 4/1996 | WIPO |
| WO9641625 | 12/1996 | WIPO |

OTHER PUBLICATIONS

Labaudiniere, R. et al., J. Med. Chem., vol. 35 (17), pp. 3156–3169 (1992).
Yuan, J.H. et al., Drug Metab. Dispos., vol. 24(10), pp. 1124–1133 (1996).
Cavallini V.G. et al., Farmaco Ed. Sci., vol. 11, pp. 378–388 (1956).
Chem. Abstracts, vol. 117(11), Abstr. No. 111411, Sep. 14, 1992.
Chem. Abstracts, vol. 126(1), Abstr. No. 302, Jan. 1, 1997.
Chem. Abstracts, vol. 53(10), Abstr. No. 9194, May 25, 1959.

*Primary Examiner*—Deborah C. Lambkin
*Attorney, Agent, or Firm*—Fitzpatrick, Cella, Harper & Scinto

[57] ABSTRACT

The present invention provides compounds having the of the formula I:

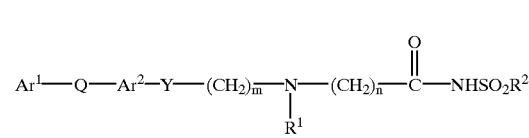

and pharmaceutically acceptable salts and stereoisomers thereof that are useful in the treatment of inflammatory diseases which are mediated by LTB₄ production, such as psoriasis, ulcerative colitis, IBD, and asthma.

30 Claims, No Drawings

LTA₄ HYDROLASE INHIBITORS

FIELD OF THE INVENTION

This invention relates generally to anti-inflammatory compounds and pharmaceutical compositions, and more particularly to anti-inflammatory compounds and compositions which are capable of inhibiting leukotriene $A_4$ hydrolase.

BACKGROUND OF THE INVENTION $LTA_4$ hydrolase is a requisite enzyme in the biosynthetic pathway leading to $LTB_4$ formation. $LTB_4$ is a proinflammatory compound. R. Lewis, et al., *N. Engl. J. Med.* 323, 645–655 (1990) have demonstrated that $LTB_4$ is a potent granulocyte agonist inducing chemotaxis, aggregation, degranulation, adherence and priming of inflammatory cells for induction by other agonists. Binding of $LTB_4$ to receptors is stereospecific with two distinct classes of binding sites. A. Lin, et al., *Prostaglandins* 28, 837–849 (1984). A high affinity site [4–5×10⁻¹⁰ M] mediates chemotaxis and chemokinesis while lower affinity sites [0.6–5×10⁻⁷ M] stimulate granular secretion and oxidative burst. The $LTB_4$ receptor is associated with a GTP-binding protein that regulates affinity and transduces signals. T. Schepers, et al., *J. Biol. Chem.* 267, 159–165 (1992). Elevated $LTB_4$ levels have been reported for many diseases. Most prominently, elevated $LTB_4$ levels have been correlated to the pathology of inflammatory bowel disease (IBD) including Crohn's disease and ulcerative colitis and in psoriasis. P. Sharon, et al., *Gastroent.* 86, 453–460; K. Lauritsen, et al., *Gastroent.* 95, 11–17 (1989); S. Brain, et al., *Br. J. Pharm.*, 83, 313–317 (1984). Other properties of $LTB_4$ which may contribute to disease processes are: stimulation of mucus secretion; stimulation of cytokine production; and the ability to act synergistically with other inflammatory mediators such as prostaglandins and cysteinyl leukotrienes thereby amplifying the inflammatory process.

B. Samuelsson, et al., *J. Biol Chem.*, 264, 19469–19472 (1989) have shown that $LTB_4$ biosynthesis from arachidonic acid involves the action of 2 enzymes, 5-lipoxygenase [5-LO] and $LTA_4$ hydrolase. 5-LO transforms arachidonic acid to 5-HPETE and subsequent formation of $LTA_4$, which is an unstable allylic epoxide intermediate which is enzymatically hydrolyzed by $LTA_4$ hydrolase to form the dihydroxy acid $LTB_4$.

$LTA_4$ hydrolase is distinct from cytosolic and microsomal epoxide hydrolases based on strict substrate requirements, product formation [5(S),12(R) vs. 5(S),6(R)] for mouse liver cytosolic epoxide hydrolase, and lack of inhibition by inhibitors of cytosolic epoxide hydrolase. $LTA_4$ hydrolase appears to be ubiquitously distributed in mammalian tissues even in cell types that do not express 5-LO, suggesting the importance of transcellular metabolism of $LTA_4$. While peptidomimetic compounds such as bestatin and captopril have been shown to exhibit $LTA_4$ hydrolase inhibitory activity, they are not able to satisfy the requirement of a small organic compound which is capable of cellular penetration. It would therefore be very advantageous to be able to provide low molecular weight inhibitors of $LTB_4$ biosynthesis which preferably exhibit oral activity in vivo at desirably low concentrations.

SUMMARY OF THE INVENTION

Applicants have now discovered that compounds of the formula (I):

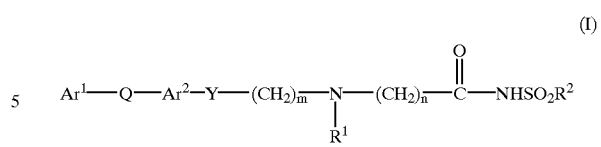

and pharmaceutically acceptable salts and stereoisomers thereof possess $LTA_4$ hydrolase inhibitor activity, wherein
$Ar^1$ is an aryl moiety selected from the group consisting of:

(i)

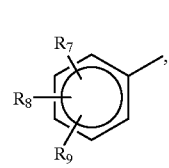

(ii)

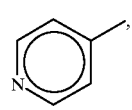

(iii)

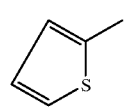

(iv)

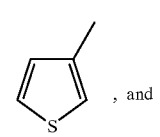, and (v)

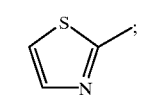;

$Ar^2$ is an aryl moiety selected from the group consisting of:
(i) phenyl, mono-, di-, or tri-substituted phenyl with the substituents selected from the group consisting of Cl, Br, F, $CF_3$, lower alkyl, lower alkoxy, $NH_2$, $NO_2$, and OH;
(ii) 2-, 4- or 5- thiazolyl,
(iii) 2-, 3- or 4-pyridinyl,
(iv) 2- or 3-thienyl, and
(v) 2- or 3-furyl;

Q is selected from the group consisting of:
(i) —O—;
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

Y is selected from the group consisting of
(i) —O—,
(ii) —S—, (iii) —NH—,
(iv) —S(O)—, and
(v) —S(O$_2$)—;

R$^1$ is hydrogen, lower alkyl, lower alkoxy or cyclic alkyl;

R$^2$ is lower alkyl or phenyl optionally substituted with lower alkyl or halogen or NR$^1$(CH$_2$)—CONHSO$_2$R$^2$ taken together forms pyrrolidino, piperidino, or piperazino substituted with (CH$_2$)$_p$—CONHSO$_2$R$^2$ and wherein the pyrrolidino, piperidino, or piperazino group is optionally substituted with one or two lower alkyl groups;

R$^7$, R$^8$, and R$^9$ are independently H, halogen, lower alkyl, lower alkoxy, NH$_2$, NO$_2$ or OH;

m is an integer from 2 to 4;

n is an integer from 2 to 6; and p is an integer from 1 to 3.

DETAILED DESCRIPTION

In one of its embodiments, the present invention entails compounds of the formula I

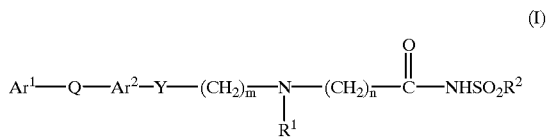

and pharmaceutically acceptable salts and stereoisomers thereof, wherein Ar$^1$, Ar$^2$, Q, Y, R$^1$, R$^2$, m and n are as defined above.

The compounds of the present invention can be prepared according to the methods disclosed and claimed in allowed U.S. application Ser. No. 08/321,183, filed Oct. 11, 1994. The disclosure of that application is hereby incorporated by reference into this specification to more fully describe the present invention.

In general, the compounds of the present invention are prepared by reacting the carboxylic acid compounds of U.S. application Ser. No. 08/321,183 and an S-aryl- or S-alkyl-sulfonamide under one of two sets of carboxylic acid activation conditions as follows:

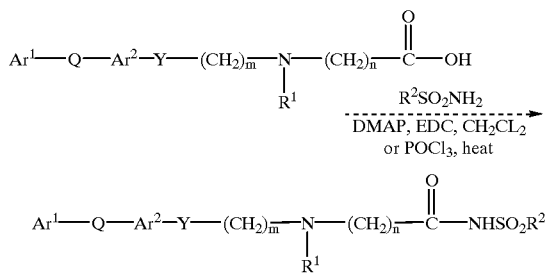

The acid and the sulfonamide can be stirred with 4-dimethylaminopyridine (DMAP) and 1-(3-dimethylaminopropyl)-3-ethylcarbodiimide hydrochloride (EDC) in dichloromethane (CH$_2$Cl$_2$). Alternatively, the acid and the sulfonamide can be heated neat with excess phosphorous oxychloride (POCl$_3$). These conditions are applicable to a broad range of carboxylic acids and sulfonamides. A more detailed description of the preparation of these compounds and preferred embodiments is provided below.

In another of its aspects, the invention entails a pharmaceutical composition comprising a pharmacologically effective amount of at least one of the compounds defined above and a pharmaceutically acceptable carrier.

In still another of its embodiments the present invention involves a method for treating a mammal exhibiting an LTB$_4$ mediated inflammatory condition comprising administering to the mammal a pharmacologically effective amount of at least one of the compounds defined above.

The term "lower alkyl" means straight or branched chain alkyl having 1 to 6 carbon atoms such as methyl, ethyl, propyl, butyl, pentyl, hexyl and the branched chain isomers thereof. The term "lower alkoxy" means straight or branched chain alkoxy having 1 to 6 carbon atoms such as methoxy, ethoxy, propoxy, butoxy, pentoxy, hexoxy and the branched chain isomers thereof. The term "allyl" as used herein means the 1-propenyl radical, —CH$_2$—CH$_2$=CH$_2$. The term "halo" means fluoro, chloro, bromo, or iodo.

Included within the classes and subclasses of compounds embraced by this invention are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The expression "pharmaceutically acceptable salts" is intended to include those salts capable of being formed with the compounds of the present invention without materially altering the chemical structure or pharmacological properties thereof. Such salts can be inorganic and organic cations or acid addition salts, including, but not limited to, sodium, potassium, calcium, ammonium, alkylammonium, quaternary ammonium, triethanolamine, lysine, hydrochloride, hydrobromide, or others known to those of ordinary skill in the art. The foregoing salts are prepared in the conventional manner by neutralization of the compounds defined above with the desired base or acid.

The compounds of the present invention can be administered to a patient in such oral dosage forms as tablets, capsules, pills, powders, granules, elixirs or syrups, as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex and medical condition of the patient; the severity of the condition to be ameliorated; and the route of administration. A physician of ordinary skill can readily determine and prescribe a "pharmaceutically effective amount" of one or more of the compounds defined above, that is, the effective amount of the compound required to prevent, treat or arrest the progress of the condition. Dosages of the compounds of the present invention will range generally between 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three to four times daily.

As used herein the phrase "LTA$_4$ hydrolase inhibitor" means a compound which is capable of exhibiting an IC$_{50}$ of less than 1 mM in an in vitro assay employing 10 μg/ml of LTA$_4$ hydrolase enzyme (specific activity 600 nMoles LTB$_4$/min/mg of enzyme) in the presence of 25 μM substrate (LTA$_4$) in a total reaction volume of 100 μl.

In the pharmaceutical compositions and methods of the present invention, at least one of the active compounds defined above or a pharmaceutically acceptable salt thereof will typically be administered in admixture with suitable pharmaceutical diluents, excipients or carriers (collectively referred to herein as "carrier materials") suitably selected with respect to the intended form of administration and consistent with conventional pharmaceutical practices. For example, the pharmaceutical compositions of this invention can be administered to a subject as oral tablets, capsules, elixirs, syrups and the like. For oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintigrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Lubricants for use in these dosage forms include boric acid, sodium benzoate, sodium acetate, sodium chloride and the like. Disintigrators include, without limitation, starch, methylcellulose, agar, bentonite, guar gum and the like.

By virtue of their activity as LTA$_4$ hydrolase inhibitors, the compounds of the invention are useful in treating inflammatory conditions mediated by LTB$_4$ production in mammals such as psoriasis, contact and atropic dermatitis, Crohn's disease, ulcerative colitis, inflammatory bowel disease, multiple sclerosis, ankylosing spondylitis, arthritis, asthma and the like. Similarly, the compounds of the invention can be used in preventing recurring inflammatory attacks. A physician or veterinarian of ordinary skill can readily determine whether a subject exhibits the inflammatory condition. A preferred utility relates to treatment of ulcerative colitis.

Examples of the compounds of the present invention include, but are not limited to, the following:

3-[Methyl[3-[4-[(2-thienyl)methyl]phenoxy]propyl]-amino]-N-(phenylsulfonyl)butanamide;

N-(Methylsulfonyl)-3-[methyl[3-[4-[(2-thienyl)-methyl]phenoxy]propyl]amino]propanamide;

3-[Ethyl[3-[4-[(2-thienyl)methyl]phenoxy]propyl]amino]-N-(methylsulfonyl)propanamide monohydrochloride;

3-[(1-methylethyl)[3-[4-[(2-thienyl)methyl]-phenoxy]propyl]-amino]-N-(methylsulfonyl)-propanamide monohydrochloride;

3-[(1-methylethyl)[3-[4-[(2-thienyl)methyl]-phenoxy]propyl]amino]-N-(phenylsulfonyl)-propanamide monohydrochloride;

3-[Ethyl[3-[4-[(3-thienyl)methyl]phenoxy]propyl]amino]-N-(methylsulfonyl)propanamide monohydrate;

3-[Ethyl[3-[4-[(3-thienyl)methyl]phenoxy]propyl]amino]-N-(methylsulfonyl)propanamide monohydrochloride;

3-[(1-methylethyl)[3-[4-[(3-thienyl)methyl]phenoxy] propyl]amino]-N-(phenylsulfonyl)-propanamide;

3-[Ethyl[3-[4-[(3-thienyl)methyl]phenoxy]propyl]amino]-N-(methylsulfonyl)propanamide monohydrochloride;

N-(methylsulfonyl)-3-[methyl[3-[4-[(3-thienyl)methyl] phenoxy]propyl]-amino]propanamide;

N-(phenylsulfonyl)-3-[propyl[3-[4-[(3-thienyl)methyl] phenoxy]propyl]-amino]propanamide monohydrochloride;

N-(methylsulfonyl)-3-[propyl[3-[4-[(3-thienyl)methyl] phenoxy]propyl]-amino]propanamide;

3-[(1-methylethyl[3-[4-[(3-thienyl)methyl]-phenoxy] propyl]-amino]-N-(phenylsulfonyl)propanamide;

3-[Methyl[3-[4-[(3-phenylmethyl)phenoxy]propyl]-amino]-N-(phenylsulfonyl)propanamide;

3-[Methyl[3-[4-[(3-phenylmethyl)phenoxy]propyl]-amino]-N-(methylsulfonyl)propanamide;

3[Cyclopropyl[3-[4-[(3-phenylmethyl)phenoxy]propyl] amino]-N-(methylsulfonyl)propanamide;

3-[(1,1-dimethylethyl)[3-[4-[(3-phenylmethyl)-phenoxy] propyl]-amino]-N-(methylsulfonyl)-propanamide;

3-[(1-methylethyl)[3-[4-[(3-phenylmethyl)-phenoxy] propyl]-amino]-N-(methylsulfonyl)-propanamide;

3-[(1-methylethyl)[3-[4-[(phenylmethyl)-phenoxy]propyl] amino]-N-(methylsulfonyl)-propanamide;

3-[Ethyl[3-[4-[(phenylmethyl)-phenoxy]propyl]-amino]-N-(methylsulfonyl)-propanamide;

3-[Ethyl[3-[4-[(phenylmethyl)-phenoxy]propyl]-amino]-N-(phenylsulfonyl)-propanamide.

The compounds of the invention are prepared from readily available starting materials by any of the following alternate processes in a conventional manner. The following reaction schemes describe methods which can be employed for preparing the compounds of the invention, including starting materials, intermediates and reaction conditions. The following terms, as used herein, have the following definitions:

| | |
|---|---|
| NMMO | N-methylmorpholine-N-oxide |
| Me | methyl |
| SitBuMe$_2$ | t-butyldimethylsilyl |
| nBuLi | n-butyllithium |
| THF | tetrahydrofuran |
| Et$_2$O | diethyl ether |
| EtOH | ethyl alcohol |
| Pd/C | palladium on carbon |
| TFA | trifluoroacetic acid |
| Et$_3$SiH | triethylsilane |
| TBAF | tetrabutylammonium fluoride |
| DMF | dimethylformamide |
| nBu$_4$NBr | tetra-n-butylammonium bromide |
| TsCl | tosylchloride or p-toluenesulfonyl-chloride |
| TsO | tosylate or p-toluenesulfonate |
| MeOH | methyl alcohol |
| AcOH | acetic acid |
| Bn | benzyl |
| DEAD | diethylazodicarboxylate |
| Ph$_3$P | triphenylphospine |
| MCPBA | metachloroperbenzoic acid |
| LAH | lithium aluminum hydride |
| TsOH | tosic acid or p-toluenesulfonic acid |
| LDA | lithium diisopropylamide |
| DSC | disuccinylcarbonate |
| nBuOH | n-butyl alcohol |
| TFAA | trifluoroacetic anhydride |
| Me$_3$SnN$_3$ | trimethyl-tin azide |
| TMS | trimethyl silyl |
| Ac$_2$O | acetic anhydride |
| Ac | acetate |
| EtOAc | ethyl acetate |
| Hep | heptane |

Scheme 1

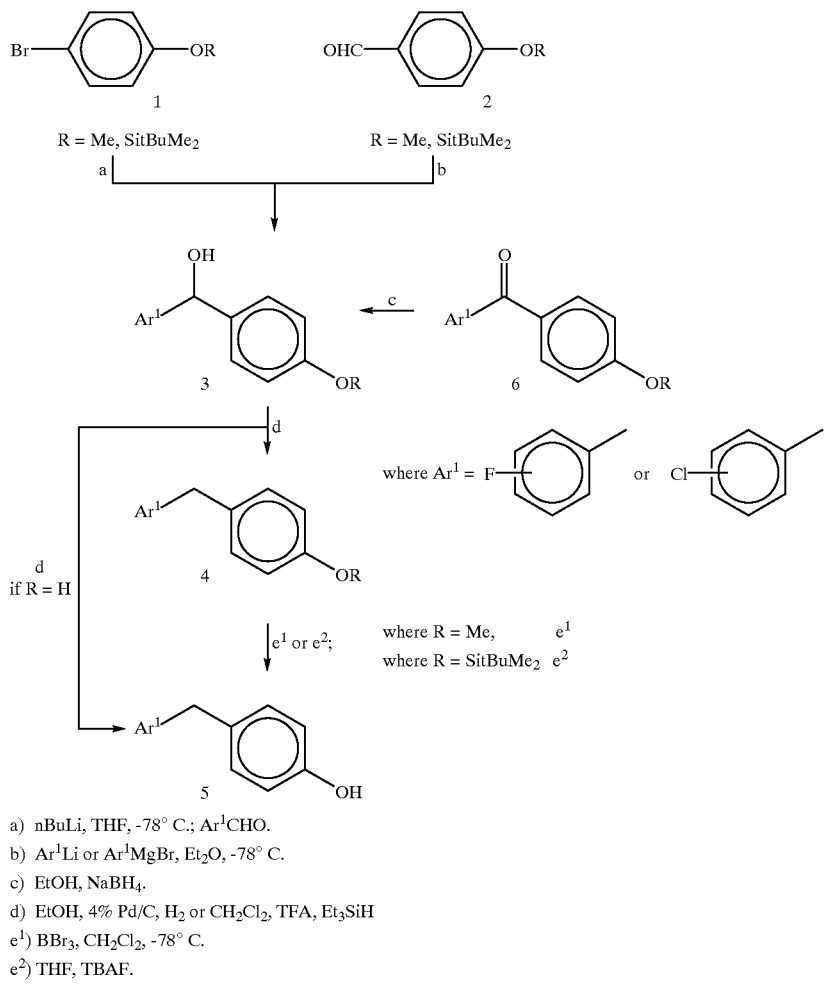

a) nBuLi, THF, -78° C.; Ar$^1$CHO.
b) Ar$^1$Li or Ar$^1$MgBr, Et$_2$O, -78° C.
c) EtOH, NaBH$_4$.
d) EtOH, 4% Pd/C, H$_2$ or CH$_2$Cl$_2$, TFA, Et$_3$SiH
e$^1$) BBr$_3$, CH$_2$Cl$_2$, -78° C.
e$^2$) THF, TBAF.

Scheme 1 shows methods for producing compounds of the formula

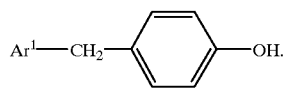

Scheme 1 shows two related precursor compounds (1, 2) which may be employed as a starting material. Compound 1 is an alkylated or silylated derivative of p-bromophenol. A convenient starting material 1 is 1-bromo-4-methoxyphenol (i.e., R is methyl). On the other hand, compound 1 may be readily provided by silylation of p-bromophenol with t-butyldiphenylsilyl chloride or other silylating agents (see, Example 2). In either event, compound 1 may be reacted with tert-butyl lithium in an ethereal solvent at low temperature, such as in THF at −78° C., and quenched with an arylaldehyde (Ar$^1$CHO) to yield compound 3. Similarly, starting from compound 2, a p-methoxybenzaldehyde or a silylated derivative of p-hydroxybenzaldehyde (see, Example 1) may be employed. Compound 2 may be reacted with an aryl lithium (Ar$^1$Li) or aryl magnesium bromide (Ar$^1$MgBr) to yield compound 3. Regardless of which route is chosen, compound 3 is reduced, e.g., by hydrogenation over palladium on carbon or with triethylsilane, to provide compound 4. Compound 4 is readily deprotected using TBAF in THF (desilylation) or using BBr$_3$ in methylene chloride at 78° C. (dealkylation) to provide compound 5.

Compounds 5 of the formula

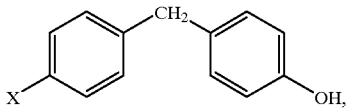

wherein X is halogen, preferably chloro or fluoro, are preferably provided by sodium borohydride reduction of a compound 6 to provide compound 3, followed by hydrogenation as described above to afford compound 5.

Scheme 2

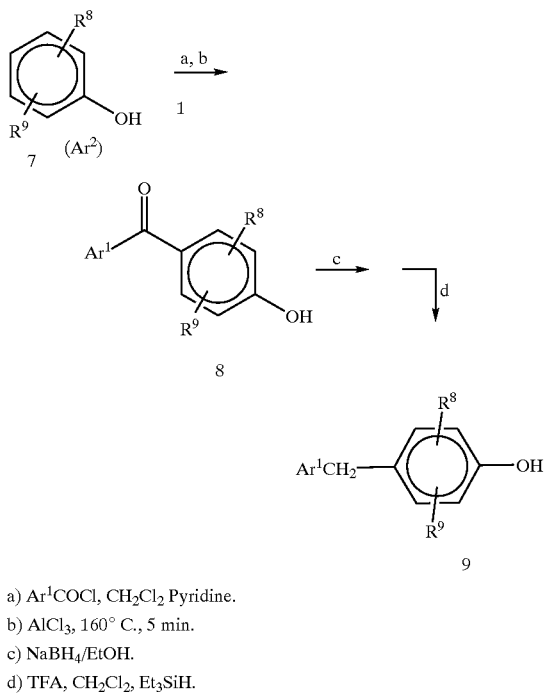

a) Ar¹COCl, CH₂Cl₂ Pyridine.
b) AlCl₃, 160° C., 5 min.
c) NaBH₄/EtOH.
d) TFA, CH₂Cl₂, Et₃SiH.

Scheme 2 depicts the preparation of compounds of formula

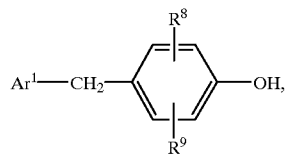

wherein $R^8$ and $R^9$ are as defined hereinbefore. In this reaction sequence, the substituted phenol 7 is reacted with a suitable aryloyl chloride to give the intermediate aryloyl ester (not shown) which is heated to a temperature of about 160° C. in the presence of AlCl₃ to promote Fries rearrangement which affords the desired compound 8, having the specifically substituted $Ar^2$ moiety. Compound 8 may be reduced utilizing the two-step reduction sequence (Scheme 1, steps (c) and (d)) to provide compound 9.

Scheme 3

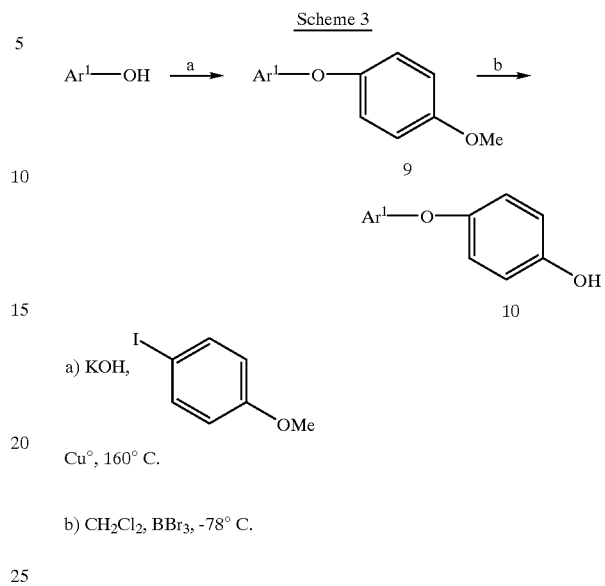

a) KOH,

[4-iodoanisole structure]

Cu°, 160° C.

b) CH₂Cl₂, BBr₃, -78° C.

Scheme 3 shows a general method for the preparation of phenols of the formula

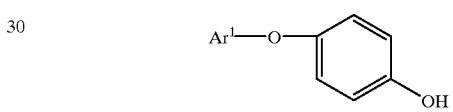

wherein $Ar^1$ is a substituted phenol. $Ar^1$ may be any substituted arylphenol which is capable of reacting with 4-iodoanisole in an Ullman coupling reaction. See, A. Moroz, et al., *Russ. Chem. Rev.* 43, 679 (1974). The Ullman reaction is carried out conventionally in the presence of activated copper or copper iodide at a temperature of about 150° C. to 200° C. to give compound 9. A presently preferred substituted phenol for providing compounds of the present invention having a substituted $Ar^1$ moiety is 4-fluorophenol. Compound 10 may be dealkylated using BBr₃ in methylene chloride at -78° C. to yield compound 10.

Scheme 4

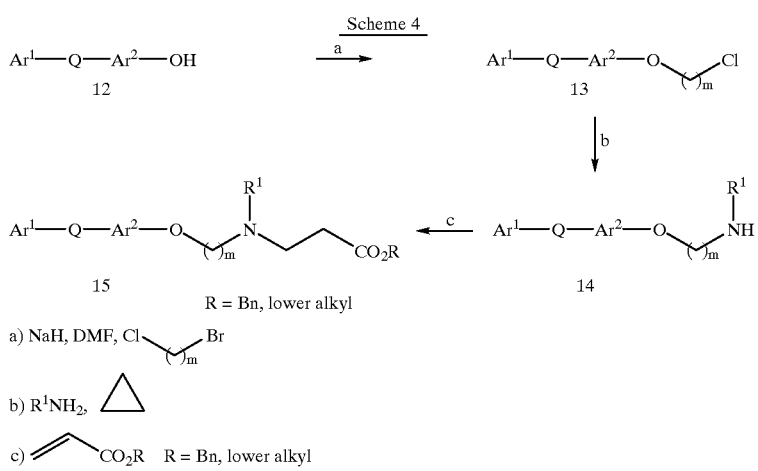

a) NaH, DMF, Cl⌒Br
b) R¹NH₂, △
c) ⌒CO₂R   R = Bn, lower alkyl

Scheme 4 depicts a general method for the preparation of carboxylic esters of the formula

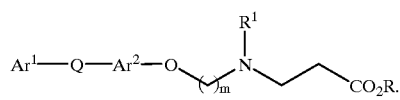

Compound 12 is reacted with Cl(CH$_2$)$_m$Br (wherein m is 2–4) in the presence of DMF and NaH to provide compound 13. Compound 13 is heated ("Δ") with an amine of the formula R$^1$NH$_2$, wherein R$^1$ is as defined hereinbefore with reference to compounds of formula I, to give compound 14. Compound 14 is reacted with benzylacrylate ester or an alkylacrylate ester to afford compound 15.

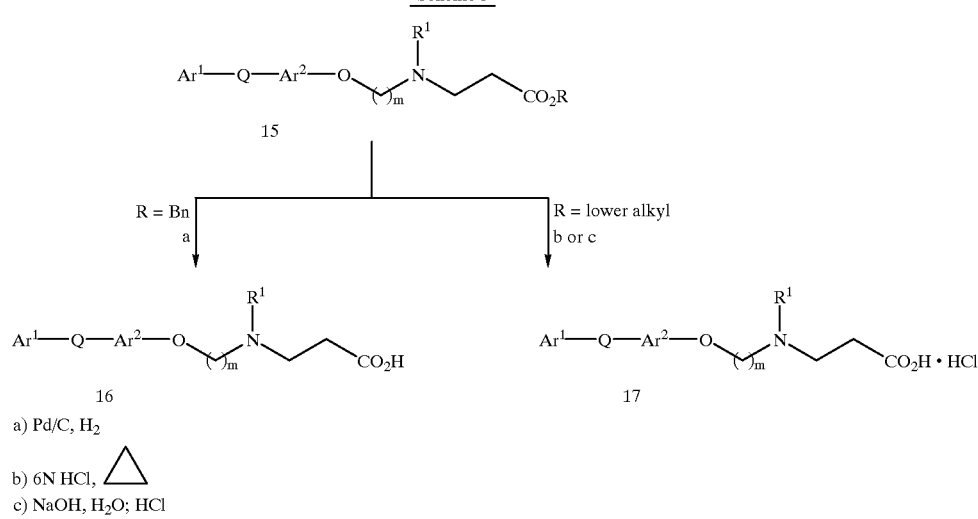

Scheme 5 shows the conversion of compound 15 which comprises an ester moiety to the corresponding acid 16 or hydrochloride 17 via one of three reactions: (1) basic hydrolysis (route c); (2) acidic hydrolysis (route b, "Δ" referring to elevated temperature), which is preferred where R is a lower alkyl; or (3) hydrogenolysis over palladium on carbon in EtOH (route a), which is especially preferred where R is benzyl.

EXAMPLE 1

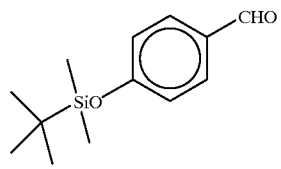

To a stirred solution of 4-hydroxybenzaldehyde (12.39, 0.1 mol, Aldrich) in DMF (50 mL) was added t-butyldimethylsilyl chloride (18.1 g, 0.12 mol) and imidazole (17 g, 0.25 mol). The mixture was stirred at room temperature for 16 hours, and diluted with pentane (200 mL). The organic layer was washed with water (3×) and brine, dried over Na$_2$SO$_4$ and concentrated in vacuo to give 25 g of the title compound as yellow oil. The resulting product had a $^1$H NMR (300 MHz) spectrum consistent with proposed structure. M+=236.

EXAMPLE 2

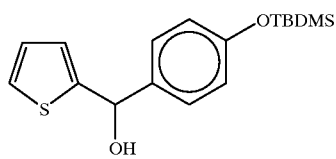

2-Bromothiophene (815 mg, 5 mmols, Aldrich) was dissolved in dry THF (20 mL) and cooled to −78° C. n-Butyllithium (3.4 mL of 1.6M solution) was added and the reaction was stirred for 2 hours under Argon. The aldehyde of Example 1 (1.18 g, 5 mmols) in THF (1 mL) was added and reaction mixture allowed to warm to room temperature over 1.5 hours. Water was added and the solution was extracted with ethyl acetate (3×30 mL). The combined organic layers were washed with brine, dried over Na$_2$SO4, filtered and concentrated in vacuo. The residue was chromatographed on silica gel using EtOAC/Heptane (20/80) as eluant to give 160 mg of compound as yellow oil. The resulting product had a $^1$H NMR (300 MHz) spectrum consistent with proposed structure.

EXAMPLE 3

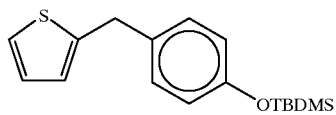

The product of Example 2 (0.5 mmol) was mixed with Et$_3$SiH (0.5 mL, Aldrich) and TFA (0.4 mL) and stirred at room temperature for 6 hours under Argon. The reaction mixture was concentrated and the residue obtained was basified with 10% aqueous NaOH solution. The reaction solution was extracted with ether (3×10 mL). The combined organic layers were washed with brine, dried (Na$_2$SO$_4$) and filtered. The filtrate was concentrated to give 160 mg product. The resulting product was fully characterized in the next step.

EXAMPLE 4

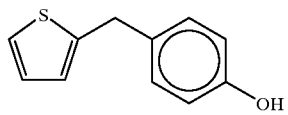

The product of Example 3 was treated with tetrabutylammonium fluoride (2.5 mL of 1M solution, Aldrich) and the mixture was stirred at room temperature for 2 hours. The solvent was removed under reduced pressure, the residue obtained was treated with water and ether. The organic layer was separated and washed two times with water and brine, dried over $Na_2SO_4$ and concentrated in vacuo to give 90 mg of the title compound as yellow oil. The resulting product was fully characterized in the next step.

EXAMPLE 5

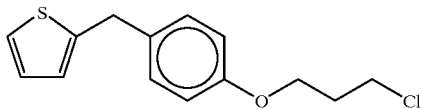

To the compound of Example 4 (1.84 g) in 50 ml dimethylformamide (DMF) was added sodium hydride (60% dispersion in mineral oil) 0.5 g (Aldrich) portionwise at room temperature during 15 min. The reaction mixture was stirred for ½ hr and 1.57 g of 1-bromo-3-chloro propane (Aldrich) in 10 ml of DMF was added dropwise during 10 min and the mixture was stirred at room temperature overnight. Diethyl ether 100 ml and water 3 ml was added to the reaction mixture and the organic phase was further washed with $H_2O$ (10 ml×2), dried, filtered, and the solvent removed in vacuo. The organic material was chromatographed over silica gel using 5% EtOAc in hexane and gave the title compound.

EXAMPLE 6

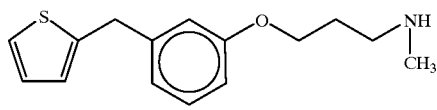

To a stirred solution of methylamine (40% solution in $H_2O$, Aldrich) (13.7 mL, 180 mmol) was added a solution of Example 2 (0.47 g, 1.8 mmol, in $CH_3CN$ 5 mL). The resulting mixture was heated to 45–50° C. for 4–5 hours and then allowed to stir at room temperature for 15 hours. The reaction was concentrated in vacuo and the aqueous residue extracted with EtOAc (2×15 mL). The organic layers were combined and acidified with 1N HCl to pH 1 at 0° C. A white precipitate was formed, and the solid was collected by vacuum filtration. The solid was washed with 1N HCl, followed by hexane to afford 0.35 g salt. The solid was dissolved in 10% NaOH (30 mL) and extracted with $Et_2O$ (2×20 mL). The organic layers were combined, dried over $Na_2SO_4$, and concentrated in vacuo to give the free amine as a clear colorless oil (0.3 g).

EXAMPLE 7

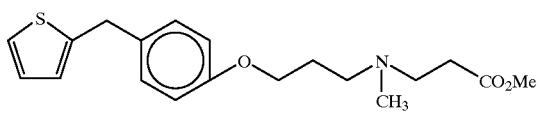

To a stirred solution of the compound of example 6 (0.30 g, 1.1 mmol in $CH_2Cl_2$ 6 mL) was added methyl acrylate (Aldrich, 0.13 mL, 1.5 mmol) at room temperature. The reaction was allowed to stir at room temperature for 17 hours, and then concentrated under a stream of nitrogen gas. The residue was purified by column chromatography using 10% $MeOH/CH_2Cl_2$ as eluant to afford 0.32 g of the title compound as a clear colorless oil. The resulting product had the following properties: Analysis calc'd for $C_{19}H_{25}NO_3S$: C, 65.58; H, 7.25; N, 4.03. Found: C, 65.38; H, 7.30; N, 3.95.

EXAMPLE 8

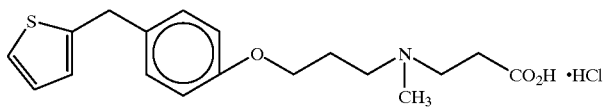

A solution of the compound of Example 7 (80 mg, 0.23 mmol) in 6 N HCl (1 mL) was heated to 70° C. for 4 hours, then concentrated in vacuo to give a white solid. The solid was slurried with $Et_2O$ and collected by vacuum filtration to give 110 mg of the title compound. The resulting product had the following properties: Analysis calc'd for $C_{18}H_{24}NO_3SCl$ 1.3 $H_2O$: C, 56.30; H, 6.01; N, 3.46. Found: C, 56.05; H, 6.22; N, 3.37.

The following carboxylic acids are referred to by number in Examples 9 through 29:

1. [chemical structure]
2. [chemical structure]
3. [chemical structure]
4. [chemical structure]
5. [chemical structure]
6. [chemical structure]
7. [chemical structure]
8. [chemical structure]
9. [chemical structure]
10. [chemical structure]

11.

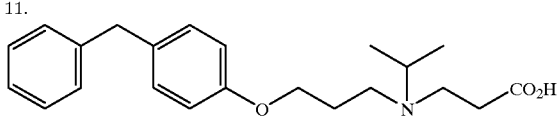

12.

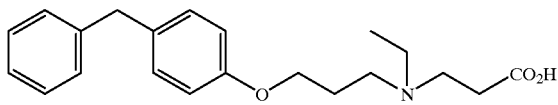

EXAMPLE 9

3-[Methyl[3-[4-[(2-thienyl)methyl]phenoxy]propyl]-amino]-N-(phenylsulfonyl)butanamide

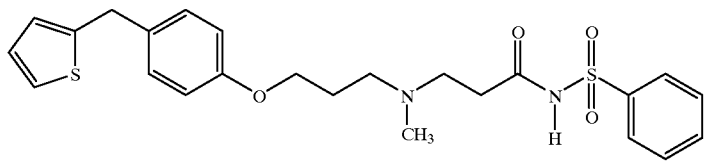

To a mixture of carboxylic acid 1 (300 mg, 0.81 mmol) in $CH_2Cl_2$ (2 mL) was added benzenesulfonamide (130 mg. 0.81 mmol) and dimethylaminopyridine (DMAP, 128 mg. 1.1 mmol). The solids went into solution and 1-(3-dimethylaminopropyl)-3-ethylcarbodiimide hydrochloride (EDC, 160 mg, 0.81 mmol) was added. The reaction was stirred at room temperature for 18 hours and then partitioned between $CH_2Cl_2$ and 10% aqeous HCl. The aqueous solution was extracted with $CH_2Cl_2$. The combined organic solution was dried ($Na_2SO_2$) and concentrated in vacuo. The residue was chromatographed on silica (85:14:1 $CH_2Cl_2$:MeOH:$NH_4OH$) to give the desired compound (29 mg,8%) as a gummy solid. Anal. calc'd for $C_{24}H_{28}N_2O_4S_2$+0.5 $H_2O$: C, 59.85; H, 6.07; N, 5.81. Found: C, 60.03; H, 6.11; N, 5.82.

EXAMPLE 10

N-(Methylsulfonyl)-3-[methyl[3-[4-[(2-thienyl)-methyl]phenoxy]propyl]amino]propanamide

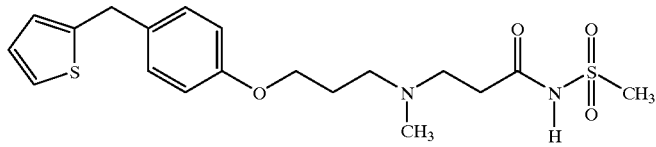

A mixture of carboxylic acid 1 (300 mg, 0.81 mmol), methanesulfonamide (77 mg, 0.81 mmol) and phosphorous oxychloride ($POCl_{3, 0.25}$ ml, 2.6 mmol) was heated at 90° C. for 3 hours. The reaction solution was cooled, diluted with $CH_2Cl_2$ and washed with 5% aqueous $NaHCO_3$ solution. The aqueous solution was extracted with $CH_2Cl_2$. The combined organic solution was dried ($Na_4SO_4$) and concentrated in vacuo. The residue was chromatographed on silica (85:14:1 $CH_2Cl_2$:MeOH:$NH_4OH$) to give the desired compound (85 mg,26%) as a viscous oil. Anal. calc'd for $C_{19}H_{26}N_2O_4S_2$+0.5 $H_2O$: C, 54.38; H, 6.48; N, 6.67. Found: C, 54.27; H, 6.59; N, 6.54.

EXAMPLE 11

3-[Ethyl[3-[4-[(2-thienyl)methyl]phenoxy]propyl]-amino]-N-(methylsulfonyl)propanamide monohydrochloride

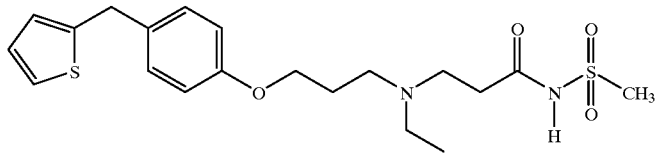

The method of Example 10 was repeated starting with carboxylic acid 2 (130 mg, 0.34 mmol), methanesulfonamide (33 mg, 0.34 mmol) and phosphorus oxychloride (0.10 mL, 1.1 mmol) which formed the desired product (48 mg, 33%) as a crystalline solid, mp 103–4° C. Anal. calc'd for $C_{20}H_{28}N_2O_4S_2+1.0$ HCl: C, 52.10; H, 6.34; N, 6.07. Found: C, 52.33; H, 6.42; N, 6.10.

EXAMPLE 12

3-[(1-methylethyl)[3-[4-[(2-thienyl)methyl-] phenoxy]propyl]-amino]-N-(methylsulfonyl)-propanamide monohydrochloride

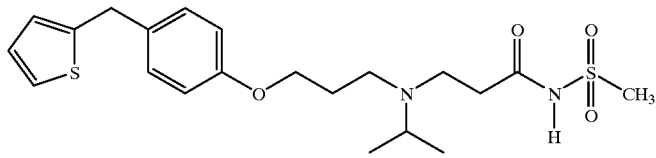

The method of Example 10 was repeated starting with carboxylic acid 3 (160 mg, 0.4 mmol), methanesulfonamide (38 mg, 0.4 mmol) and phosphorus oxychloride (0.12 mL, 1.3 mmol) which formed the desired product (62 mg, 37%) as a viscous oil. Anal. calc'd for $C_{21}H_{30}N_2O_4S_2+1.0$ HCl: C, 53.09; H, 6.58; N, 5.89. Found: C, 52.90; H, 6.68; N, 5.83.

EXAMPLE 13

3-[(1-methylethyl)[3-[4-[(2-thienyl)methyl-] phenoxy]propyl]amino]-N-(phenylsulfonyl)-propanamide, monohydrochloride

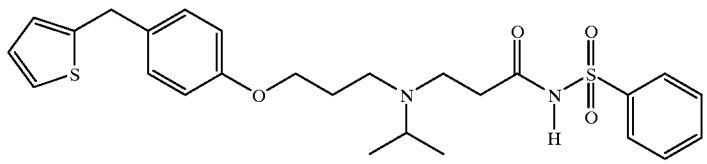

The method of Example 10 was repeated starting with carboxylic acid 3 (170 mg, 0.42 mmol), benzenesulfonamide (67 mg, 0.42 mmol) and phosphorus oxychloride (0.13 mL, 1.35 mmol) which formed the desired product (80 mg, 37%) as a viscous oil.

EXAMPLE 14

3-[Ethyl[3-[4-[(3-thienyl)methyl]phenoxy]propyl]-amino]-N-(methylsulfonyl)propanamide monohydrate

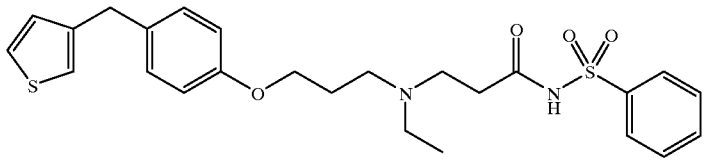

Carboxylic acid 5 (290 mg, 0.83 mmol) was dissolved in 10 mL of $CH_2Cl_2$ and benzensulfonamide, EDC and DMAP were added. The reaction mixture was stirred under nitrogen overnight and the reaction mixture was quenched with water and extracted 3 times with $CH_2Cl_2$. The organic layers were dried over anhydrous $MgSO_4$ and concentrated to the crude product which was purified by flash chromatography on silica gel using 20/79/1 $EtOH/CH_2Cl_2/NH_4OH$ as eluent to give the product (170 mg). Anal. calc'd for $C_{25}H_{30}N_2S_2O_4 \cdot H_2O$: C, 59.50; H, 6.39; N, 5.55. Found: C, 59.18; H, 6.04; N, 5.64.

EXAMPLE 15

3-[Ethyl[3-[4-[(3-thienyl)methyl]phenoxy]propyl]-amino]-N-(methylsulfonyl)propanamide monohydrochloride

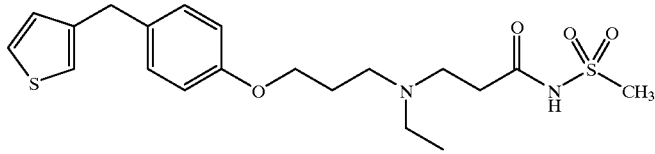

Carboxylic acid 5 (478 mg, 1.38 mmol) was dissolved in 10 ml $CH_2Cl_2$, and methanesulfonamide (131 mg, 1.38 mmol), EDC (272 mg, 1.31 mmol) and DMAP (219 mg, 1.79 mmol) were added. The reaction mixture was stirred under nitrogen overnight. The reaction mixture was partitioned between $CH_2Cl_2$ and water and the organic layer was dried over $MgSO_4$ and concentrated in vacuo to give an oil which was purified by chromatography using 15/84/1 $EtOH/CH_2Cl_2/NH_4OH$ as eluent to give the desired product (59 mg). Anal. calc'd for $C_{20}H_{28}N_2O_4S_2 \cdot HCl$: C, 52.10; H, 6.34; N, 6.08. Found: C, 51.82; H, 6.38; N, 5.73.

EXAMPLE 16

3-[(1-methylethyl)[3-[4-[(3-thienyl)methyl]-phenoxy]propyl]amino]-N-(phenylsulfonyl)-propanamide

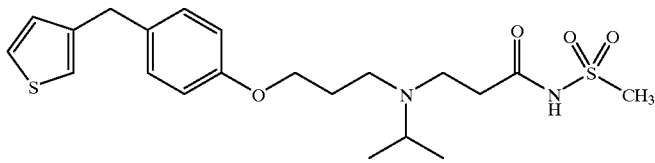

Carboxylic acid 7 (320 mg, 0.88 mmol), methanesulfonamide (84.3 mg, 0.88 mmol) and 2 mL of phosphorus oxychloride ($POCl_3$) were heated at 90° C. for 5 h. The reaction mixture was quenched with water and neutralized with aq. $Na_2CO_3$. The mixture was extracted with $CH_2Cl_2$ and the organic layer separated, dried over $MgSO_4$ and concentrated to give an oil which was purified by chromatography using 4/95/1 $EtOH/CH_2Cl_2/NH_4OH$ as eluent to give 138 mg of product. Anal. calc'd for $C_{21}H_{30}N_2O_4S_2 \cdot 0.8$ HCl: C, 53.92; H, 6.64; N, 5.99. Found: C, 53.74; H, 6.85; N, 5.78.

EXAMPLE 17

3-[Ethyl[3-[4-[(3-thienyl)methyl]phenoxy]propyl]-amino]-N-(methylsulfonyl)propanamide monohydrochloride

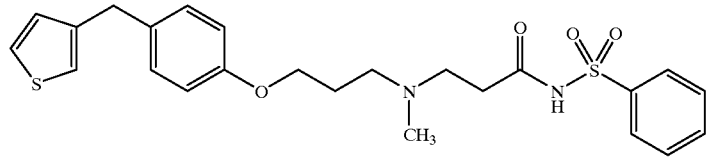

Carboxylic acid 4 (300 mg, 0.9 mmol) was converted to the sulfonamide using the EDC conditions as in Example 15 to give 150 mg of product: Anal. calc'd for $C_{24}H_{28}N_2O_4S_2 \cdot 0.5 H_2O$: C, 59.85; H, 6.07; N, 5.80. Found: C, 59.64; H, 5.94; N, 5.80.

EXAMPLE 18

N-(methylsulfonyl)-3-[methyl[3-[4-[(3-thienyl)methyl]phenoxy]propyl]-amino]propanamide

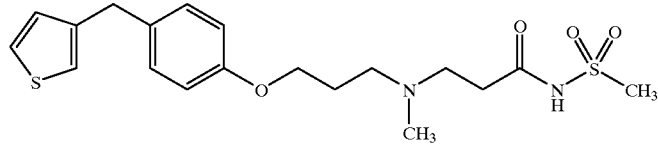

Carboxylic acid 4 (389 mg, 1.17 mmol) was converted to the sulfonamide using the $POCl_3$ conditions as in Example 16 to give 101 mg of product; Anal. calc'd for $Cl_{19}H_{26}N_2O_4S_2 \cdot 0.4 H_2O$; C, 54.63; H, 6,47; N, 6.71. Found: C, 54.56; H, 6.66; N, 6.76.

EXAMPLE 19

N-(phenylsulfonyl)-3-[propyl[3-[4-[(3-thienyl)methyl]phenoxy]propyl]-amino]propanamide monohydrochloride

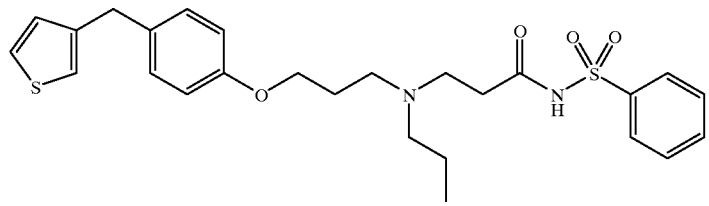

Carboxylic acid 6 (304 mg, 0.81 mmol) was converted to the sulfonamide using the POCl$_3$ conditions as in Example 16 to give 83 mg of desired product: Anal. calc'd for $C_{21}H_{30}N_2O_4S_2$•0.8 H$_2$O: C, 55.68; H, 7.03; N, 6.18. Found: C, 55.43; H, 7.08; N, 6.04.

EXAMPLE 20

N-(methylsulfonyl)-3-[propyl[3-[4-[(3-thienyl)methyl]phenoxy]propyl]-amino]propanamide

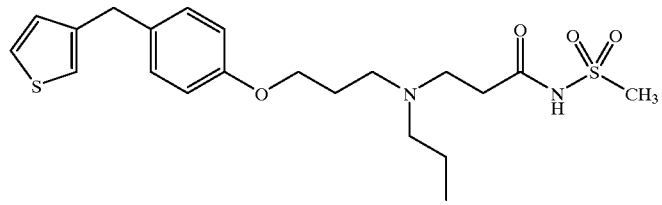

Carboxylic acid 6 (200 mg, 0.532 mmol) was converted to the sulfonamide using the POCl$_3$ conditions as in Example 16 to give 80 mg of desired product; Anal. calc'd for $C_{26}H_{33}N_2O_4S_2Cl$•0.1 H$_2$O: C, 57.94; H, 6.21; N, 5.20. Found: C, 57.64; H, 5.97; N, 5.06.

EXAMPLE 21

3-[(1-methylethyl[3-[4-[(3-thienyl)methyl]phenoxy]propyl]-amino]-N-(phenylsulfonyl)propanamide

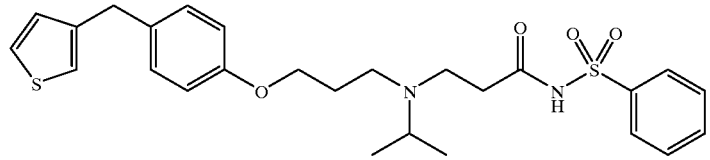

Carboxylic acid 7 (304 mg, 0.84 mmol) was converted to the sulfonamide using the EDC conditions as in Example 15 to give 40 mg of product; Anal. calc'd for $C_{26}H_{32}N_2O_4S_2$•0.3 H$_2$O: C, 61.71; H, 6.49; N, 5.54. Found: C, 61.35; H, 6.03; N, 5.39.

EXAMPLE 22

3-[Methyl[3-[4-[(3-phenylmethyl)phenoxy]propyl]-amino]-N-(phenylsulfonyl)propanamide

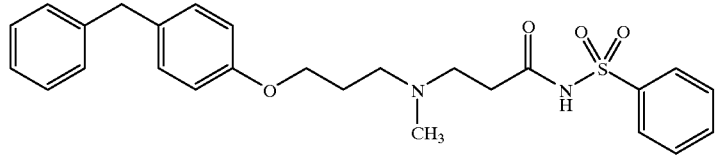

Carboxylic acid 8 (500 mg, 1.37 mmol) was converted to the phenylsulfonamide using the EDC conditions as in Example 15 to give 130 mg of product: Anal. calc'd for $C_{26}H_{30}N_2SO_4$: C, 66.93; H, 6.48; N, 6.00. Found: C, 66.68; H, 6.46; N, 5.92.

EXAMPLE 23

3-[Methyl[3-[4-[(3-phenylmethyl)phenoxy]propyl]-amino]-N-(methylsulfonyl)propanamide

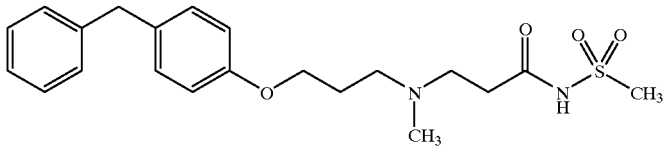

Carboxylic acid 8 (500 mg, 1.37 mmol) was converted to the methylsulfonamide using the EDC conditions as in Example 15 to give 150 mg of product; Anal. calc'd for $C_{21}H_{28}N_2O_4S \cdot 0.9\ H_2O$: C, 59.95; H 7.14; N, 6.66. Found: C, 59.58; H, 6.99; N, 6.47.

EXAMPLE 24

3-[Cyclopropyl[3-[4-[(3-phenylmethyl)phenoxy]propyl]-amino]-N-(methylsulfonyl)propanamide

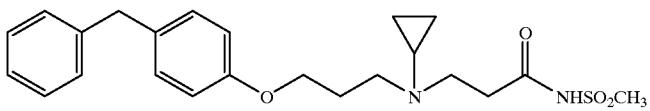

To the carboxylic acid 9 (391 mg) was added phosphorus oxychloride (0.4 mL) and methanesulfonamide (110 mg) and the mixture heated to 90° C. for 2 h. The mixture was cooled and extracted with 20 mL of ethyl acetate. The organic extract was concentrated and chromatographed over silica gel using 30:70:1—EtOH:EtOAc:NH$_4$OH to give the desired product, 0.2 g. Anal. Calc'd for $C_{23}H_{30}N_2O_4S \cdot 0.8H_2O$: C, 62.08; H, 7.16; N, 6.30. Found: C, 61.83; H, 7.18; N, 6.21.

EXAMPLE 25

3-[(1,1-dimethylethyl)[3-[4-[(3-phenylmethyl)-phenoxy]propyl]-amino]-N-(methylsulfonyl)-propanamide

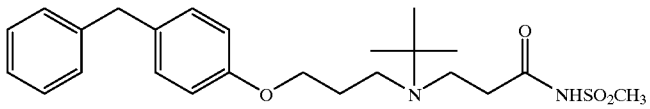

To carboxylic acid 10 (40 mg) was added POCl$_3$ (0.05 mL), methanesulfonamide (10 mg) and the mixture heated to 90° C. as described in Example 16. The reaction mixture was chromatographed over silica gel using 30:70:1 EtOH:EtOAc:NH$_4$OH, 1H NMR (MeOD) δ 1.51 (s, 9H), 2.26–2.40 (m, 2H), 2.7–2.75 (m, 2H), 3.08 (s,3H), 3.35–3.42 (m,4H), 3.92 (s, 2H), 4.05–4.12 (m, 2H), 6.82–6.87 (m, 2H), 7.09–7.31 (m, 7H) 7.57 (s,1H).

EXAMPLE 26

3-[(1-methylethyl)[3-[4-[(3-phenylmethyl)-phenoxy]propyl]-amino]-N-(methylsulfonyl)-propanamide

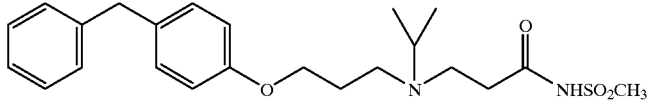

Carboxylic acid 11 was converted to the methylsulfonamide using the POCl$_3$ procedure described in Example 25.

EXAMPLE 27

3-[(1-methylethyl)[3-[4-[(phenylmethyl)-phenoxy]propyl]amino]-N-(methylsulfonyl)-propanamide

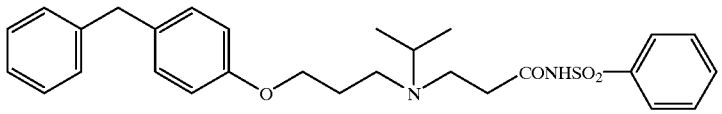

Carboxylic acid 11 (760 mg) was converted to the desired product using the EDC/DMAP procedure as in Example 15 to give the sulfonamide as a white solid.

EXAMPLE 28

3-[Ethyl[3-[4-[(phenylmethyl)-phenoxy]propyl]-amino]-N-(methylsulfonyl)-propanamide

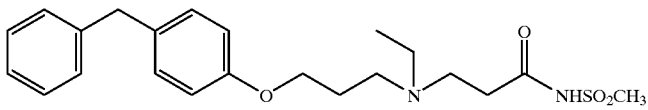

Carboxylic acid 12 (760 mg) was converted to the methylsulfonamide using the $POCl_3$ procedure as in Example 25 to give 350 mg of desired material.

EXAMPLE 29

3-[Ethyl[3-[4-[(phenylmethyl)-phenoxy]propyl]-amino]-N-(phenylsulfonyl)-propanamide

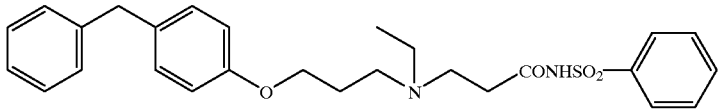

Carboxylic acid 12 (670 mg) was converted to the phenylsulfonamide using the EDC/DMAP procedure as in Example 15 to give 0.3 g of sulfonamide.

LTA Hydrolase Methods

The following Table presents data demonstrating the pharmacological activity of the LTA hydrolase inhibitors of the present invention. One or more of three different assays, (1) an in vitro LTA hydrolase enzyme assay, (2) a human whole blood assay utilizing calcium ionophore stimulation, and (3) a murine ex vivo assay utilizing calcium ionophore stimulation were employed to determine the level of LTA hydrolase inhibitor activity.

Recombinant Human LTA Hydrolase Assay for LTA Hydrolase Inhibitor Activity

Compounds of the present invention were tested for LTA hydrolase inhibitor activity against recombinant human LTA hydrolase (rhLTAH). Recombinant human LTA hydrolase-encoding vectors were prepared and used to express rhLTAH essentially as described by J. Gierse, et al., *Protein Expression and Purification*, 4, 358–366 (1993). Briefly, LTA hydrolase encoding DNA was amplified by polymerase chain reaction using a pair of oligonucleotide primers based on the nucleotide sequence from the 5'-end, and the complement of the 3'-end, of the coding region of the LTA hydrolase gene, the nucleotide sequence of which gene is known. (See, C. Funk, et al., Proc. Natl. Acad. Sci. USA 84, 6677–6681 (1987)). A λgt11 human placental cDNA library (Clonetech, Palo Alto, Calif.) provided the nucleic acid template. The LTA hydrolase encoding region had a length of about 1.9 kb. The amplified 1.9 kb DNA was isolated and cloned into the genomic baculovirus, *Autographa californica* nuclear polyderosis virus (AcNPC) DNA, and the baculovirus expression vector was transfected into Spodoptera frugiperda Sf-9 cells employing the calcium phosphate co-precipitation method (see, M. Summers, et al., Tex. Agric. Exp. Stn. Bull. 1555, 1–57 (1987). Recombinant $LTA_4$ hydrolase enzyme was purified from the transfected Sf-9 cells essentially as described by J. Gierse, et al., supra.

One or more predetermined amounts of a compound of the invention were incubated in assay buffer (0.1 M potassium phosphate, 5 mg/ml fatty acid free BSA, 10% DMSO, pH 7.4) for 10 minutes at room temperature with 250 ng of recombinant $hLTA_4H$ to allow binding, if any, between the enzyme and inhibitor. The stock enzyme solution was 1 mg/m. $LTA_4$ hydrolase, 50 mM Tris, pH 8.0, 150 mM NaCl, 2.5 mM beta-mercaptoethanol, 50% glycerol. The specific activity of the enzyme was about 650 nMoles/min/mg. $LTA_4$ (i.e., substrate) was prepared from the methyl ester of $LTA_4$ (Biomol, Inc., Plymouth Meeting, Pa.) by treating the methyl ester with 30 molar equivalents of LiOH at room temperature for 18 hours. The $LTA_4$ substrate in its free acid form was kept frozen at −80° C. until needed. $LTA_4$ (free acid) was thawed and diluted in assay buffer (minus DMSO) to a concentration of 350 ng/ml and 25 µl (8ng) of $LTA_4$ substrate was added to the reaction mixture (total volume of reaction mixture=200 µl at time zero. Each reaction was carried out at room temperature for 10 minutes. The reaction was stopped by diluting 25 µl of the reaction mixture with 500 µl of the assay buffer without DMSO. $LTA_4$ was quantified in the diluted sample by a commercially available enzyme-linked immunoassay [Caymen Chemical Col. Ann Arbor, Mich.] using the method recommended in the manufacturer's instructions and compared to the amount of $LTA_4$ produced in a negative control (i.e., essentially identical conditions except without addition of an inhibitor compound). The $IC_{50}$ was routinely calculated from the data produced.

$LTB_4$ and Thromboxane Production by Calcium Ionophore Stimulated Human Blood for $LTB_4$ Hydrolase Inhibitor Activity Human blood, collected in heparin-containing Vacutainer tubes, was diluted 1:4 with RPMI-1640 media and 200 µl of the diluted blood was added into each of a 96-well microtiter plate. One or more concentrations of the leukotriene $A_4$ hydrolase inhibitor compounds being tested were prepared (diluted in DMSO) and 2 μl added and gently mixed with the diluted whole blood. After incubating for 15 minutes at 37° C. in a humidified incubator, calcium ionophore A13187 (Sigma Chemical Co., St. Louis, Mo.) was added to a final concentration of 20 mcg/ml and the incubation continued under the same conditions for an additional 10 minutes to allow $LTB_4$ formation. The reaction was terminated by centrifugation (833 g, 10 minutes at 4° C.) and supernatant were analyzed for $LTB_4$ and thromboxane by commercially available enzyme-linked immunoassays (Caymen Chemical Co., Ann Arbor, Mich.) according to the manufacturer's instructions. The IC50 of each test compound was determined from the amount of inhibition of $LTB_4$ production as compared to an essentially identical assay in which no inhibitor compound was present.

Ex Vivo $LTB_4$ and Thromboxane Production by Calcium Ionophore Stimulated Mouse Blood for $LTB_4$ Hydrolase Inhibitor Activity Leukotriene $A_4$ hydrolase inhibitor compounds of the present invention were diluted to a predetermined concentration in phosphate buffered saline containing 2% DMSO and 1% Tween 80. The compounds were administered by oral garage to adult male outbred mice weighing approximately 20–30 gm at a dose of 10 mg/kg body weight. (Compounds given at a dose of 50 mg/kg body weight are designated in following Table by the symbol, *) Sixty (60) minutes after administration of an $LTA_4$ inhibitor compound of the invention, blood was collected (into heparin-containing tubes) from the retroorbital sinus. The heparinized blood was added to the wells of a microtiter plate along with an equal volume of RPMI-1640 media, and calcium ionophore A23187 was added to a final concentration of 20 mcg/ml. The mixture was incubated for 10 minutes at 37° C. in a humidified incubator. The reaction was terminated by centrifugation (833 g. 10 minutes at 4° C.). Supernatant were analyzed for $LTB_4$ and thromboxane by commercially available enzyme-linked immunoassays [Caymen Chemical Co., Ann Arbor, Mich.] in accordance with the manufacturer's instructions. The percent inhibition was determined by comparison to animals treated identically except that the solution administered by oral gavage was devoid of inhibitor compound.

$LTA_4$ HYDROLASE INHIBITOR ACTIVITY

| Ex. # | Inhibition of Recombinant Human $LTA_4$ Hydrolase Assay $IC_{50}$ (μM) $LTA_4$ | Inhibition of Calcium Ionophore-induced $LTB_4$ Production in Human Blood $IC_{50}$ (μM) HWB | Murine Ex Vivo $LTB_4$ Inhibition % I $LTB_4$/ at 1 hour after administration of 10 mg/kg (* indicates administration of 50 mg/kg) |
|---|---|---|---|
| 9  | <0.0005 | 0.079 | 87 |
| 10 | 0.0005  | 0.061 | 93 |
| 11 | 0.033   | 0.066 | 86 |
| 12 | 0.012   | 0.08  | 68 |
| 13 | 0.0023  | 0.04  | 50 |
| 14 | 0.011   | 0.082 | 87 |
| 15 | 0.43    | 0.23  | 79 |
| 16 | 0.45    | 0.2   | 85 |
| 17 | 0.0005  | 0.13  | 93 |
| 18 | 0.02    | 0.19  | 94 |
| 19 | 0.09    | 0.075 | 45 |
| 20 | 0.15    | 0.15  | 56 |
| 21 | 0.09    | 0.15  | 60 |
| 22 | 0.001   | 0.075 | 94 |
| 23 | 0.0013  | 0.07  | 100 |
| 24 | 2.16    | 2.71  | — |
| 25 | 0.1     | 0.11  | 45 |
| 26 | 0.16    | 0.22  | 81 |
| 27 | 0.047   | 0.1   | 44 |
| 28 | 0.54    | 0.18  | 89 |
| 29 | 0.079   | 0.13  | 65 |

"—" means Not Determined

What is claimed is:

1. A compound having the structure:

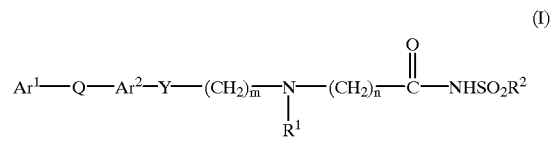

(I)

and pharmaceutically acceptable salts and stereoisomers thereof wherein $Ar^1$ is an aryl moiety selected from the group. consisting of:

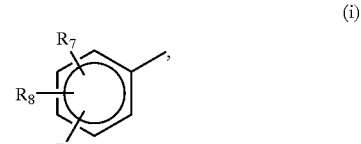

(i)

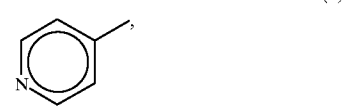

(ii)

(iii)

(iv)

, and

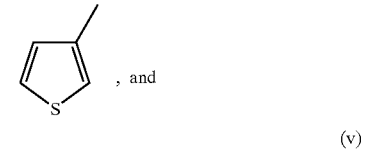

(v)

;

$Ar^2$ is an aryl moiety selected from the group consisting of:

(i) phenyl, mono-, di-, or tri-substituted phenyl with the substituents selected from the group. consisting of Cl, Br, F, CF$_3$, lower alkyl, lower alkoxy, NH$_2$, NO$_2$, and OH;
(ii) 2-, 4- or 5- thiazolyl,
(iii) 2-, 3- or 4-pyridinyl,
(iv) 2- or 3-thienyl, and
(v) 2- or 3-furyl;

Q is selected from the group consisting of:
(i) —O—;
(ii) —CH$_2$—,
(iii) —OCH$_2$—,
(iv) —CH$_2$O—,
(v) —NH—;
(vi) —NHCH$_2$—,
(vii) —CH$_2$NH—,
(viii) —CF$_2$—,
(ix) —CH=CH—,
(x) —CH$_2$CH$_2$—, and
(xi) carbon-carbon single bond;

Y is selected from the group consisting of
(i) —O—,
(ii) —S—,
(iii) —NH—,
(iv) —S(O)—, and
(v) —S(O$_2$)—;

R$^1$ is hydrogen, lower alkyl, lower alkoxy or cyclic alkyl;
R$^2$ is lower alkyl or phenyl optionally substituted with lower alkyl or halogen or NR$^1$(CH$_2$)—CONHSO$_2$R$^2$ taken together forms pyrrolidino, piperidino, or piperazino substituted with (CH$_2$)$_p$—CONHSO$_2$R$^2$ and wherein the pyrrolidino, piperidino, or piperazino group is optionally substituted with one or two lower alkyl groups;
R$_7$, R$_8$, and R$_9$ are independently H, halogen, lower alkyl, lower alkoxy, NH$_2$, NO$_2$ or OH;
m is an integer from 2 to 4;
n is an integer from 2 to 6; and
p is an integer from 1 to 3.

2. The compound of claim 1 wherein Ar$^2$ is chosen from the group consisting of phenyl, mono-, di-, and tri-substituted phenyl with the substituents selected from the group consisting of Cl, Br, F, CF$_3$, lower alkyl, lower alkoxy, NH$_2$, NO$_2$, and OH.

3. The compound of claim 2 wherein Ar$^1$ has the structure:

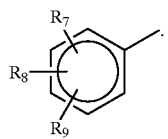

4. The compound of claim 2 wherein Ar$^1$ has the structure:

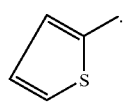

5. The compound of claim 2 wherein Ar$^1$ has the structure:

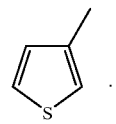

6. The compound of claims 3, 4 or 5 wherein Q is —CH$_2$—.
7. The compound of claim 6 wherein Y is —O—.
8. The compound of claim 7 wherein R$^2$ is lower alkyl.
9. The compound of claim 7 wherein R$^2$ is chosen from the group consisting of phenyl, mono-, di-, and tri-substituted phenyl wherein the subtitutents are chosen from the group consisting of alkyl and halogen.
10. The compound of claim 1 chosen from the group consisting of:

3-[Methyl[3-[4-[(2-thienyl)methyl]phenoxy]propyl]-amino]-N-(phenylsulfonyl)butanamide;

N-(Methylsulfonyl)-3-[methyl[3-[4-[(2-thienyl)-methyl]phenoxy]propyl]amino]propanamide;

3-[Ethyl[3-[4-[(2-thienyl)methyl]phenoxy]propyl]-amino]-N-(methylsulfonyl)propanamide monohydrochloride;

3-[(1-methylethyl)[3-[4-[(2-thienyl)methyl]-phenoxy]propyl]-amino]-N-(methylsulfonyl)-propanamide monohydrochloride;

3-[(1-methylethyl)[3-[4-[(2-thienyl)methyl]-phenoxy]propyl]-amino]-N-(phenylsulfonyl)-propanamide monohydrochloride;

3-[Ethyl[3-[4-[(3-thienyl)methyl]phenoxy]propyl]-amino]-N-(methylsulfonyl)propanamide monohydrate;

3-[Ethyl[3-[4-[(3-thienyl)methyl]phenoxy]propyl]-amino]-N-(methylsulfonyl)propanamide monohydrochloride;

3-[(1-methylethyl)[3-[4-[(3-thienyl)methyl]-phenoxy] propyl]amino]-N-(phenylsulfonyl)-propanamide;

3-[Ethyl[3-[4-[(3-thienyl)methyl]phenoxy]propyl]-amino]-N-(methylsulfonyl)propanamide monohydrochloride;

N-(methylsulfonyl)-3-[methyl[3-[4-[(3thienyl)methyl] phenoxy]propyl]-amino]propanamide;

N-(phenylsulfonyl)-3-[propyl[3-[4-[(3-thienyl)methyl] phenoxy]propyl]-amino]propanamide monohydrochloride;

N-(methylsulfonyl)-3-[propyl[3-[4-[(3-thienyl)methyl] phenoxy]propyl]-amino]propanamide;

3-[(1-methylethyl[3-[4-[(3-thienyl)methyl]-phenoxy] propyl]-amino]-N-(phenylsulfonyl)propanamide;

3-[Methyl[3-[4-[(3-phenylmethyl)phenoxy]propyl]-amino]-N-(phenylsulfonyl)propanamide;

3-[Methyl[3-[4-[(3-phenylmethyl)phenoxy]propyl]-amino]-N-(methylsulfonyl)propanamide;

3-[Cyclopropyl[3-[4-[(3-phenylmethyl)phenoxy]propyl]-amino]-N-(methylsulfonyl)propanamide;

3-[(1,1-dimethylethyl)[3-[4-[(3-phenylmethyl)-phenoxy] propyl]-amino]-N-(methylsulfonyl)-propanamide;

3-[(1-methylethyl)[3-[4-[(3-phenylmethyl)-phenoxy] propyl]-amino]-N-(methylsulfonyl)-propanamide;

3-[(1-methylethyl)[3-[4-[(phenylmethyl)-phenoxy] propyl]amino]-N-(methylsulfonyl)-propanamide;

3-[Ethyl[3-[4-[(phenylmethyl)-phenoxy]propyl]-amino]-N-(methylsulfonyl)-propanamide;

3-[Ethyl[3-[4-[(phenylmethyl)-phenoxy]propyl]-amino]-
N-(phenylsulfonyl)-propanamide.

11. A pharmaceutical composition comprising a compound of the formula I:

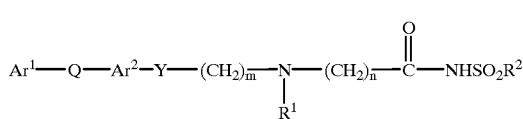

and pharmaceutically acceptable salts and stereoisomers thereof and a pharmaceutically acceptable carrier, wherein $Ar^1$ is an aryl moiety selected from the group consisting of:

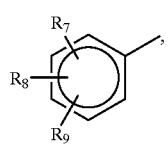 (i)

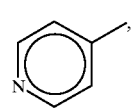 (ii)

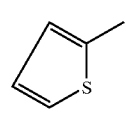 (iii)

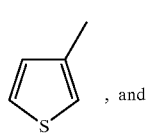 (iv)

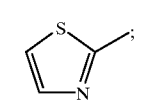 (v)

$Ar^2$ is an aryl moiety selected from the group consisting of:
(i) phenyl, mono-, di-, or tri-substituted phenyl with the substituents selected from the group consisting of Cl, Br, F, $CF_3$, lower alkyl, lower alkoxy, $NH_2$, $NO_2$, and OH;
(ii) 2-, 4- or 5- thiazolyl,
(iii) 2-, 3- or 4-pyridinyl,
(iv) 2- or 3-thienyl, and
(v) 2- or 3-furyl;

Q is selected from the group consisting of:
(i) —O—;
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

Y is selected from the group consisting of
(i) —O—,
(ii) —S—,
(iii) —NH—,
(iv) —S(O)—, and
(v) —$S(O_2)$—;

$R^1$ is hydrogen, lower alkyl, lower alkoxy or cyclic alkyl;
$R^2$ is lower alkyl or phenyl optionally substituted with lower alkyl or halogen or $NR^1(CH_2)$—$CONHSO_2R^2$ taken together forms pyrrolidino, piperidino, or piperazino substituted with $(CH_2)_p$—$CONHSO_2R^2$ and wherein the pyrrolidino, piperidino, or piperazino group is optionally substituted with one or two lower alkyl groups;
$R_7$, $R_8$, and $R_9$ are independently H, halogen, lower alkyl, lower alkoxy, $NH_2$, $NO_2$ or OH;
m is an integer from 2 to 4;
n is an integer from 2 to 6; and
p is an integer from 1 to 3.

12. The pharmaceutical composition of claim 11 wherein in the compound $Ar^2$ is is chosen from the group consisting of phenyl, mono-, di-, and tri-substituted phenyl with the substituents selected from the group consisting of Cl, Br, F, $CF_3$, lower alkyl, lower alkoxy, $NH_2$, $NO_2$, and OH.

13. The pharmaceutical composition of claim 12 wherein in the compound $Ar^1$ has the structure:

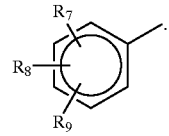

14. The pharmaceutical composition of claim 12 wherein in the compound $Ar^1$ has the structure:

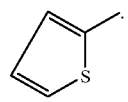

15. The pharmaceutical composition of claim 12 wherein in the compound $Ar^1$ has the structure:

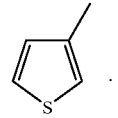

16. The pharmaceutical composition of claims 13, 14 or 15 wherein in the compound Q is —$CH_2$—.

17. The pharmaceutical composition of claim 16 wherein in the compound Y is —O—.

18. The pharmaceutical composition of claim 17 wherein in the compound $R^2$ is lower alkyl.

19. The pharmaceutical composition of claim 17 wherein in the compound $R^2$ is chosen from the group consisting of phenyl, mono-, di-, and tri-substituted phenyl wherein the subtitutents are chosen from the group consisting of alkyl and halogen.

20. The pharmaceutical composition of claim 11 wherein the compound is chosen from the group consisting of:
3-[Methyl[3-[4-[(2-thienyl)methyl]phenoxy]propyl]-amino]-N-(phenylsulfonyl)butanamide;

N-(Methylsulfonyl)-3-[methyl[3-[4-[(2-thienyl)-methyl]phenoxy]propyl]amino]propanamide;

3-[Ethyl[3-[4-[(2-thienyl)methyl]phenoxy]propyl]amino]-N-(methylsulfonyl)propanamide monohydrochloride;

3-[(1-methylethyl)[3-[4-[(2-thienyl)methyl]-phenoxy]propyl]-amino]-N-(methylsulfonyl)-propanamide monohydrochloride;

3-[(1-methylethyl)[3-[4-[(2-thienyl)methyl]-phenoxy]propyl]amino]-N-(phenylsulfonyl)-propanamide monohydrochloride;

3-[Ethyl[3-[4-[(3-thienyl)methyl]phenoxy]propyl]amino]-N-(methylsulfonyl)propanamide monohydrate;

3-[Ethyl[3-[4-[(3-thienyl)methyl]phenoxy]propyl]amino]-N-(methylsulfonyl)propanamide monohydrochloride;

3-[(1-methylethyl)[3-[4-[(3-thienyl)methyl]-phenoxy]propyl]amino]-N-(phenylsulfonyl)-propanamide;

3-[Ethyl[3-[4-[(3-thienyl)methyl]phenoxy]propyl]amino]-N-(methylsulfonyl)propanamide monohydrochloride;

N-(methylsulfonyl)-3-[methyl[3-[4-[(3-thienyl)methyl]phenoxy]propyl]-amino]propanamide;

N-(phenylsulfonyl)-3-[propyl[3-[4-[(3-thienyl)methyl]phenoxy]propyl]-amino]propanamide monohydrochloride;

N-(methylsulfonyl)-3-[propyl[3-[4-[(3-thienyl)methyl]phenoxy]propyl]-amino]propanamide;

3-[(1-methylethyl[3-[4-[(3-thienyl)methyl]-phenoxy]propyl]-amino]-N-(phenylsulfonyl)propanamide;

3-[Methyl[3-[4-[(3-phenylmethyl)phenoxy]propyl]-amino]-N-(phenylsulfonyl)propanamide;

3-[Methyl[3-[4-[(3-phenylmethyl)phenoxy]propyl]-amino]-N-(methylsulfonyl)propanamide;

3-[Cyclopropyl[3-[4-[(3-phenylmethyl)phenoxy]propyl]-amino]-N-(methylsulfonyl)propanamide;

3-[(1,1-dimethylethyl)[3-[4-[(3-phenylmethyl)-phenoxy]propyl]-amino]-N-(methylsulfonyl)-propanamide;

3-[(1-methylethyl)[3-[4-[(3-phenylmethyl)-phenoxy]propyl]-amino]-N-(methylsulfonyl)-propanamide;

3-[(1-methylethyl)[3-[4-[(phenylmethyl)-phenoxy]propyl]amino]-N-(methylsulfonyl)-propanamide;

3-[Ethyl[3-[4-[(phenylmethyl)-phenoxy]propyl]-amino]-N-(methylsulfonyl)-propanamide;

3-[Ethyl[3-[4-[(phenylmethyl)-phenoxy]propyl]-amino]-N-(phenylsulfonyl)-propanamide.

21. A method for treating an $LTB_4$-mediated inflammatory disease comprising administering to a mammal in need of treatment a therapeutically effective amount of a compound of the formula I:

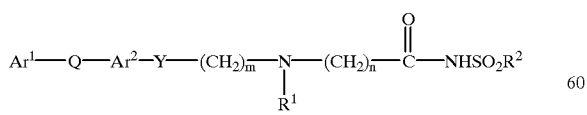

and pharmaceutically acceptable salts and stereoisomers thereof wherein $Ar^1$ is an aryl moiety selected from the group consisting of:

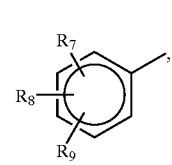  (i)

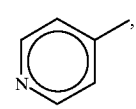  (ii)

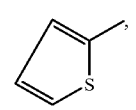  (iii)

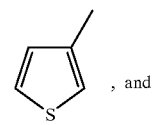  , and  (iv)

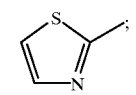  ;  (v)

$Ar^2$ is an aryl moiety selected from the group consisting of:
(i) phenyl, mono-, di-, or tri-substituted phenyl with the substituents selected from the group consisting of Cl, Br, F, $CF_3$, lower alkyl, lower alkoxy, $NH_2$, $NO_2$, and OH;
(ii) 2-, 4- or 5- thiazolyl,
(iii) 2-, 3- or 4-pyridinyl,
(iv) 2- or 3-thienyl, and
(v) 2- or 3-furyl;

Q is selected from the group consisting of:
(i) —O—;
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

Y is selected from the group consisting of
(i) —O—,
(ii) —S—,
(iii) —NH—,
(iv) —S(O)—, and
(v) —$S(O_2)$—;

$R^1$ is hydrogen, lower alkyl, lower alkoxy or cyclic alkyl;

$R^2$ is lower alkyl or phenyl optionally substituted with lower alkyl or halogen or $NR^1(CH_2)$—$CONHSO_2R^2$ taken together forms pyrrolidino, piperidino, or piperazino substituted with $(CH_2)_p$—$CONHSO_2R^2$ and wherein the pyrrolidino, piperidino, or piperazino group is optionally substituted with one or two lower alkyl groups;

$R_7$, $R_8$, and $R_9$ are independently H, halogen, lower alkyl, lower alkoxy, $NH_2$, $NO_2$ or OH;

m is an integer from 2 to 4;
n is an integer from 2 to 6; and
p is an integer from 1 to 3.

22. The method of claim 21 wherein in the compound $Ar^2$ is chosen from the group consisting of phenyl, mono-, di-, and tri-substituted phenyl with the substituents selected from the group consisting of Cl, Br, F, $CF_3$, lower alkyl, lower alkoxy, $NH_2$, $NO_2$, and OH.

23. The method of claim 22 wherein in the compound $Ar^1$ has the structure:

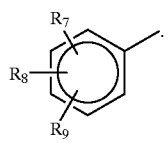

24. The method of claim 22 wherein in the compound $Ar^1$ has the structure:

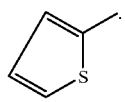

25. The method of claim 22 wherein in the compound $Ar^1$ has the structure:

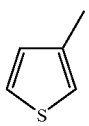

26. The method of claims 23, 24 or 25 wherein in the compound Q is —$CH_2$—.

27. The method of claim 26 wherein in the compound Y is —O—.

28. The method of claim 27 wherein in the compound $R^2$ is lower alkyl.

29. The method of claim 27 wherein in the compound $R^2$ is chosen from the group consisting of phenyl, mono-, di-, and tri-substituted phenyl wherein the subtitutents are chosen from the group consisting of alkyl and halogen.

30. The method of claim 21 wherein the compound is chosen from the group consisting of:

3-[Methyl[3-[4-[(2-thienyl)methyl]phenoxy]propyl]-amino]-N-(phenylsulfonyl)butanamide;

N-(Methylsulfonyl)-3-[methyl[3-[4-[(2-thienyl)-methyl]phenoxy]propyl]amino]propanamide;

3-[Ethyl[3-[4-[(2-thienyl)methyl]phenoxy]propyl]-amino]-N-(methylsulfonyl)propanamide monohydrochloride;

3-[(1-methylethyl)[3-[4-[(2-thienyl)methyl]-phenoxy]propyl]-amino]-N-(methylsulfonyl)-propanamide monohydrochloride;

3-[(1-methylethyl)[3-[4-[(2-thienyl)methyl]-phenoxy]propyl]amino]-N-(phenylsulfonyl)-propanamide monohydrochloride;

3-[Ethyl[3-[4-[(3-thienyl)methyl]phenoxy]propyl]-amino]-N-(methylsulfonyl)propanamide monohydrate;

3-[Ethyl[3-[4-[($^3$-thienyl)methyl]phenoxy]propyl]-amino]-N-(methylsulfonyl)propanamide monohydrochloride;

3-[(1-methylethyl)[3-[4-[(3-thienyl)methyl]-phenoxy]propyl]amino]-N-(phenylsulfonyl)-propanamide;

3-[Ethyl[3-[4-[(3-thienyl)methyl]phenoxy]propyl]-amino]-N-(methylsulfonyl)propanamide monohydrochloride;

N-(methylsulfonyl)-3-[methyl[3-[4-[(3-thienyl)methyl]phenoxy]propyl]-amino]propanamide;

N-(phenylsulfonyl)-3-[propyl[3-[4-[(3-thienyl)methyl]phenoxy]propyl]-amino]propanamide monohydrochloride;

N-(methylsulfonyl)-3-[propyl[3-[4-[(3-thienyl)methyl]phenoxy]propyl]-amino]propanamide;

3-[(1-methylethyl[3-[4-[(3-thienyl)methyl]-phenoxy]propyl]-amino]-N-(phenylsulfonyl)propanamide;

3-[Methyl[3-[4-[(3-phenylmethyl)phenoxy]propyl]-amino]-N-(phenylsulfonyl)propanamide;

3-[Methyl[3-[4-[(3-phenylmethyl)phenoxy]propyl]-amino]-N-(methylsulfonyl)propanamide;

3-[Cyclopropyl[3-[4-[(3-phenylmethyl)phenoxy]propyl]-amino]-N-(methylsulfonyl)propanamide;

3-[(1,1-dimethylethyl)[3-[4-[(3-phenylmethyl)-phenoxy]propyl]-amino]-N-(methylsulfonyl)-propanamide;

3-[(1-methylethyl)[3-[4-[(3-phenylmethyl)-phenoxy]propyl]-amino]-N-(methylsulfonyl)-propanamide;

3-[(1-methylethyl)[3-[4-[(phenylmethyl)-phenoxy]propyl]amino]-N-(methylsulfonyl)-propanamide;

3-[Ethyl[3-[4-[(phenylmethyl)-phenoxy]propyl]-amino]-N-(methylsulfonyl)-propanamide;

3-[Ethyl[3-[4-[(phenylmethyl)-phenoxy]propyl]-amino]-N-(phenylsulfonyl)-propanamide.

* * * * *